United States Patent
Whitman

(10) Patent No.: US 7,803,151 B2
(45) Date of Patent: Sep. 28, 2010

(54) SYSTEM AND METHOD FOR CALIBRATING A SURGICAL INSTRUMENT

(75) Inventor: Michael P. Whitman, New Hope, PA (US)

(73) Assignee: Power Medical Interventions, LLC, Mansfield, MA (US)

( * ) Notice: Subject to any disclaimer, the term of this patent is extended or adjusted under 35 U.S.C. 154(b) by 1080 days.

(21) Appl. No.: 10/309,532

(22) Filed: Dec. 4, 2002

(65) Prior Publication Data

US 2003/0125717 A1    Jul. 3, 2003

Related U.S. Application Data

(60) Provisional application No. 60/337,544, filed on Dec. 4, 2001.

(51) Int. Cl.
*A61B 17/00* (2006.01)

(52) U.S. Cl. .................. 606/1; 600/101; 600/117; 600/118; 600/160; 702/150; 702/151; 702/158; 227/175.1; 227/181.1

(58) Field of Classification Search .......... 600/101, 600/117, 118, 160; 606/1, 167, 180, 177, 606/42, 170; 702/150–151, 158; 227/175.1–182.1
See application file for complete search history.

(56) References Cited

U.S. PATENT DOCUMENTS

| | | | |
|---|---|---|---|
| 1,798,902 A | 3/1931 | Raney |
| 2,031,682 A | 2/1936 | Wappler et al. |
| 2,174,219 A | 9/1939 | Balma |
| 2,246,647 A | 6/1941 | Vancura |
| 2,419,045 A | 4/1947 | Whittaker |
| 2,725,628 A | 12/1955 | O'Neilly et al |
| 3,120,845 A | 2/1964 | Homer |
| 3,193,165 A | 7/1965 | Akhalaya et al. |
| 3,252,643 A | 5/1966 | Strekopytov et al. |
| 3,253,643 A | 5/1966 | Gudheim |
| 3,275,211 A | 9/1966 | Hirsch et al. |
| 3,315,863 A | 4/1967 | O'Dea |
| 3,317,105 A | 5/1967 | Astafiev et al. |
| 3,388,847 A | 6/1968 | Kasulin et al. |
| 3,490,576 A | 1/1970 | Alessi et al. |
| 3,490,675 A | 1/1970 | Green et al. |
| 3,494,533 A | 2/1970 | Green et al. |
| 3,499,591 A | 3/1970 | Green |
| 3,552,626 A | 1/1971 | Astafiev et al. |
| 3,589,589 A | 6/1971 | Akopov |
| 3,593,903 A | 7/1971 | Astafiev et al. |
| 3,638,652 A | 2/1972 | Kelley |
| 3,643,851 A | 2/1972 | Green |

(Continued)

FOREIGN PATENT DOCUMENTS

DE    2330182    1/1975

(Continued)

*Primary Examiner*—Matthew J Kasztejna

(57) ABSTRACT

A calibration system for a surgical instrument. The calibration system includes an actuator, such as a motor system and a flexible shaft. The calibration system also includes a surgical instrument actuatable by the actuator. The calibration system also include calibration data corresponding to the surgical instrument. A processor is configured to process the calibration data for determining a position of the surgical instrument. The calibration system may include a sensor configured to provide a signal corresponding to a movement of the actuator, the processor being further configured to process the signal for determining a position of the surgical instrument.

17 Claims, 7 Drawing Sheets

U.S. PATENT DOCUMENTS

| | | | |
|---|---|---|---|
| 3,662,939 A | 5/1972 | Bryan | |
| 3,675,688 A | 7/1972 | Bryan et al. | |
| 3,692,224 A | 9/1972 | Astafiev et al. | |
| 3,717,294 A | 2/1973 | Green | |
| 3,735,762 A | 5/1973 | Bryan et al. | |
| 3,777,538 A | 12/1973 | Weatherly et al. | |
| 3,788,303 A | 1/1974 | Hall | |
| 3,795,034 A | 3/1974 | Strekopytov et al. | |
| 3,815,476 A | 6/1974 | Green et al. | |
| 3,819,100 A | 6/1974 | Noiles et al. | |
| 3,837,555 A | 9/1974 | Green | |
| 3,844,289 A | 10/1974 | Noiles et al. | |
| 3,882,854 A | 5/1975 | Hulka et al. | |
| 3,892,228 A | 7/1975 | Mitsui | |
| 3,935,981 A | 2/1976 | Akopov et al. | |
| 3,949,924 A | 4/1976 | Green | |
| RE28,932 E | 8/1976 | Noiles et al. | |
| 4,014,492 A | 3/1977 | Rothfuss | |
| 4,027,510 A | 6/1977 | Hiltebrandt | |
| 4,060,089 A | 11/1977 | Noiles | |
| 4,064,881 A | 12/1977 | Meredith | |
| 4,086,926 A | 5/1978 | Green et al. | |
| 4,092,986 A | 6/1978 | Schneiderman | |
| 4,111,206 A | 9/1978 | Vishnevsky et al. | |
| 4,169,476 A | 10/1979 | Hiltebrandt | |
| 4,198,982 A | 4/1980 | Fortner et al. | |
| 4,202,479 A | 5/1980 | Razgulov et al. | |
| 4,202,480 A | 5/1980 | Annett | |
| 4,207,873 A | 6/1980 | Kruy | |
| 4,207,898 A | 6/1980 | Becht | |
| 4,244,372 A | 1/1981 | Kapitanov et al. | |
| 4,261,244 A | 4/1981 | Becht et al. | |
| 4,273,129 A | 6/1981 | Boebel | |
| 4,296,881 A | 10/1981 | Lee | |
| 4,304,236 A | 12/1981 | Conta et al. | |
| 4,319,576 A | 3/1982 | Rothfuss | |
| 4,325,377 A | 4/1982 | Boebel | |
| 4,349,028 A | 9/1982 | Green | |
| 4,354,628 A | 10/1982 | Green | |
| 4,383,634 A | 5/1983 | Green | |
| 4,391,401 A | 7/1983 | Moshofsky | |
| 4,402,445 A | 9/1983 | Green | |
| 4,461,305 A | 7/1984 | Cibley | |
| 4,473,077 A | 9/1984 | Noiles et al. | |
| 4,489,875 A | 12/1984 | Crawford et al. | |
| 4,506,670 A | 3/1985 | Crossley | |
| 4,506,671 A | 3/1985 | Green | |
| 4,513,746 A | 4/1985 | Aranyi et al. | |
| 4,519,532 A | 5/1985 | Foslien | |
| 4,534,352 A | 8/1985 | Korthoff | |
| 4,566,620 A | 1/1986 | Green et al. | |
| 4,573,622 A | 3/1986 | Green et al. | |
| 4,589,416 A | 5/1986 | Green | |
| 4,589,582 A | 5/1986 | Bilotti | |
| 4,591,085 A | 5/1986 | Di Giovanni | |
| 4,607,638 A | 8/1986 | Crainich | |
| 4,633,861 A | 1/1987 | Chow et al. | |
| 4,633,874 A | 1/1987 | Chow et al. | |
| 4,643,190 A | 2/1987 | Heimberger | |
| 4,657,017 A | 4/1987 | Sorochenko | |
| 4,664,305 A | 5/1987 | Blake, III et al. | |
| 4,669,471 A | 6/1987 | Hayashi | |
| 4,688,555 A | 8/1987 | Wardle | |
| 4,705,038 A * | 11/1987 | Sjostrom et al. | 606/180 |
| 4,714,187 A | 12/1987 | Green | |
| 4,715,502 A | 12/1987 | Salmon | |
| 4,728,020 A | 3/1988 | Green et al. | |
| 4,763,669 A | 8/1988 | Jaeger | |
| 4,767,044 A | 8/1988 | Green | |
| 4,805,823 A | 2/1989 | Rothfuss | |
| 4,819,853 A | 4/1989 | Green | |
| 4,841,888 A | 6/1989 | Mills et al. | |
| 4,848,637 A | 7/1989 | Pruitt | |
| 4,858,608 A | 8/1989 | McQuilkin | |
| 4,863,088 A | 9/1989 | Redmond et al. | |
| 4,887,612 A | 12/1989 | Esser et al. | |
| 4,907,973 A | 3/1990 | Hon | |
| 4,919,152 A | 4/1990 | Ger | |
| 4,932,960 A | 6/1990 | Green et al. | |
| 4,941,623 A | 7/1990 | Pruitt | |
| 4,944,093 A | 7/1990 | Falk | |
| 4,944,443 A | 7/1990 | Oddsen et al. | |
| 4,955,959 A | 9/1990 | Tompkins et al. | |
| 4,977,900 A | 12/1990 | Fehling et al. | |
| 4,978,049 A | 12/1990 | Green | |
| 4,991,764 A | 2/1991 | Mericle | |
| 4,995,877 A * | 2/1991 | Ams et al. | 606/180 |
| 5,018,657 A | 5/1991 | Pedlick et al. | |
| 5,031,814 A | 7/1991 | Tompkins et al. | |
| 5,071,430 A | 12/1991 | de Salis et al. | |
| 5,108,391 A | 4/1992 | Flachenecker et al. | |
| 5,119,983 A | 6/1992 | Green et al. | |
| 5,156,315 A | 10/1992 | Green et al. | |
| 5,157,837 A | 10/1992 | Rose | |
| 5,158,222 A | 10/1992 | Green | |
| 5,170,925 A | 12/1992 | Madden et al. | |
| 5,173,133 A | 12/1992 | Morin et al. | |
| 5,217,460 A | 6/1993 | Knoepfler | |
| 5,253,793 A | 10/1993 | Green | |
| 5,254,117 A | 10/1993 | Rigby et al. | |
| 5,258,004 A | 11/1993 | Bales et al. | |
| 5,275,609 A | 1/1994 | Pingleton et al. | |
| 5,290,303 A | 3/1994 | Pingleton et al. | |
| 5,292,053 A | 3/1994 | Bilotti et al. | |
| 5,295,990 A | 3/1994 | Levin | |
| 5,300,087 A | 4/1994 | Knoepfler | |
| 5,312,434 A | 5/1994 | Crainich | |
| 5,318,221 A | 6/1994 | Green et al. | |
| 5,320,627 A | 6/1994 | Sorensen et al. | |
| 5,322,055 A | 6/1994 | Davison et al. | |
| 5,324,288 A | 6/1994 | Billings et al. | |
| 5,324,300 A | 6/1994 | Elias et al. | |
| 5,330,471 A | 7/1994 | Eggers | |
| 5,336,229 A | 8/1994 | Noda | |
| 5,342,381 A | 8/1994 | Tidemand | |
| 5,352,222 A | 10/1994 | Rydell | |
| 5,352,223 A | 10/1994 | McBrayer et al. | |
| 5,352,235 A | 10/1994 | Koros et al. | |
| 5,356,408 A | 10/1994 | Rydell | |
| 5,364,409 A | 11/1994 | Kuwabara et al. | |
| 5,366,133 A | 11/1994 | Geiste | |
| 5,366,476 A | 11/1994 | Noda | |
| 5,391,144 A * | 2/1995 | Sakurai et al. | 604/22 |
| 5,391,156 A | 2/1995 | Hildwein et al. | |
| 5,395,369 A | 3/1995 | McBrayer et al. | |
| 5,396,900 A | 3/1995 | Slater et al. | |
| 5,397,046 A | 3/1995 | Savage et al. | |
| 5,400,267 A * | 3/1995 | Denen et al. | 702/59 |
| 5,425,705 A | 6/1995 | Evard et al. | |
| 5,425,745 A | 6/1995 | Green et al. | |
| 5,456,684 A | 10/1995 | Schmidt et al. | |
| 5,464,404 A | 11/1995 | Abela et al. | |
| 5,465,894 A | 11/1995 | Clark et al. | |
| 5,476,206 A | 12/1995 | Green et al. | |
| 5,482,054 A | 1/1996 | Slater et al. | |
| 5,496,317 A | 3/1996 | Goble et al. | |
| 5,514,134 A | 5/1996 | Rydell et al. | |
| 5,518,164 A * | 5/1996 | Hooven | 227/5 |
| 5,520,634 A | 5/1996 | Fox et al. | |
| 5,527,313 A | 6/1996 | Scott et al. | |
| 5,535,937 A | 7/1996 | Boiarski et al. | |
| 5,562,677 A | 10/1996 | Hildwein et al. | |
| 5,569,274 A | 10/1996 | Rapacki et al. | |
| 5,573,543 A | 11/1996 | Akopov et al. | |

| | | |
|---|---|---|
| 5,578,052 A | 11/1996 | Koros et al. |
| 5,580,067 A | 12/1996 | Hamblin et al. |
| 5,603,443 A | 2/1997 | Clark et al. |
| 5,607,094 A | 3/1997 | Clark et al. |
| 5,617,857 A * | 4/1997 | Chader et al. ............... 600/424 |
| 5,618,303 A | 4/1997 | Marlow et al. |
| 5,618,307 A | 4/1997 | Donlon et al. |
| 5,626,607 A | 5/1997 | Malecki et al. |
| 5,651,780 A * | 7/1997 | Jackson et al. ................. 606/1 |
| 5,665,100 A | 9/1997 | Yoon |
| 5,667,526 A | 9/1997 | Levin |
| 5,688,269 A | 11/1997 | Newton et al. |
| 5,732,871 A | 3/1998 | Clark et al. |
| 5,735,848 A | 4/1998 | Yates et al. |
| 5,735,849 A | 4/1998 | Baden et al. |
| 5,735,861 A | 4/1998 | Peifer et al. |
| 5,741,285 A | 4/1998 | McBrayer et al. |
| 5,823,956 A | 10/1998 | Roth et al. |
| 5,855,590 A | 1/1999 | Malecki et al. |
| 5,893,875 A | 4/1999 | O'Connor et al. |
| 5,913,842 A | 6/1999 | Boyd et al. |
| 6,017,354 A * | 1/2000 | Culp et al. .................. 606/170 |
| 6,022,325 A | 2/2000 | Menachem et al. |
| 6,037,724 A * | 3/2000 | Buss et al. .................... 318/71 |
| 6,090,123 A * | 7/2000 | Culp et al. .................. 606/180 |
| 6,110,188 A | 8/2000 | Narciso, Jr. |
| 6,302,311 B1 * | 10/2001 | Adams et al. ............ 227/176.1 |
| 6,331,181 B1 * | 12/2001 | Tierney et al. ............... 606/130 |
| 6,368,340 B2 | 4/2002 | Malecki et al. |
| 6,370,411 B1 * | 4/2002 | Osadchy et al. ............. 600/372 |
| 6,434,507 B1 * | 8/2002 | Clayton et al. .............. 702/152 |
| 6,517,478 B2 * | 2/2003 | Khadem ..................... 600/117 |
| 6,790,217 B2 | 9/2004 | Schulze et al. |
| 6,793,652 B1 * | 9/2004 | Whitman et al. ................ 606/1 |
| 6,899,538 B2 * | 5/2005 | Matoba ....................... 433/114 |
| 7,273,483 B2 * | 9/2007 | Wiener et al. ............... 606/169 |
| 2001/0016750 A1 | 8/2001 | Malecki et al. |
| 2001/0031975 A1 | 10/2001 | Whitman et al. |

FOREIGN PATENT DOCUMENTS

| | | |
|---|---|---|
| DE | 3114135 | 10/1982 |
| EP | 41022 | 12/1981 |
| EP | 293123 | 1/1988 |
| EP | 324166 | 7/1989 |
| EP | 324637 | 7/1989 |
| EP | 365153 | 4/1990 |
| EP | 369324 | 5/1990 |
| EP | 373762 | 6/1990 |
| EP | 630612 | 12/1994 |
| EP | 639349 | 2/1995 |
| EP | 679367 | 11/1995 |
| EP | 552423 | 1/1998 |
| EP | 581400 | 5/2000 |
| EP | 484677 | 7/2000 |
| GB | 1352554 | 5/1974 |
| GB | 1452185 | 10/1976 |
| GB | 2048685 | 12/1980 |
| GB | 2165559 | 4/1986 |
| NL | 7711347 | 4/1979 |
| RU | 659146 | 4/1979 |
| WO | WO 9006085 | 6/1990 |

* cited by examiner

といった,

SYSTEM AND METHOD FOR CALIBRATING A SURGICAL INSTRUMENT

CLAIM OF PRIORITY

This application claims the benefit of priority of U.S. Patent Application Ser. No. 60/337,544, filed on Dec. 4, 2001, which is expressly incorporated herein by reference in its entirety.

CROSS-REFERENCE TO RELATED APPLICATIONS

This application incorporates by reference in its entirety U.S. application Ser. No. 09/723,715, filed on Nov. 28, 2000, U.S. application Ser. No. 09/836,781, filed on Apr. 17, 2001, U.S. application Ser. No. 09/887,789, filed on Jun. 22, 2001, U.S. application Ser. No. 09/324,451, filed on Jun. 2, 1999, which issued as U.S. Pat. No. 6,315,184 on Nov. 13, 2002, U.S. application Ser. No. 09/324,452, filed on Jun. 2, 1999, which issued as U.S. Pat. No. 6,443,973 on Sep. 3, 2002, U.S. application Ser. No. 09/351,534, filed on Jul. 12, 1999, which issued as U.S. Pat. No. 6,264,087 on Jul. 24, 2001, U.S. application Ser. No. 09/510,923, filed on Feb. 22, 2000, U.S. application Ser. No. 09/510,927, filed on Feb. 22, 2000, U.S. application Ser. No. 09/510,932, filed on Feb. 22, 2000, U.S. application Ser. No. 09/510,926, filed on Feb. 22, 2000, U.S. application Ser. No. 09/510,931, filed on Feb. 22, 2000, U.S. application Ser. No. 09/510,933, filed on Feb. 22, 2000, U.S. application Ser. No. 09/999,6342, filed on Mar. 15, 2002, and U.S. application Ser. No. 09/836,781, filed on Apr. 17, 2001.

FIELD OF THE INVENTION

The present invention relates to a system and method for calibrating a surgical instrument. More particularly, the present invention relates to a system and method for calibrating the movement of components of a surgical instrument.

BACKGROUND OF THE INVENTION

Surgeons utilize various surgical instruments for performing surgical procedures. One surgical instrument commonly used is a surgical linear clamping and stapling instrument. Such a stapler is typically used for joining and repairing tissue. Another type of surgical instrument is a circular stapler, used to perform a circular anastomosis. These staplers, and many other types of surgical instruments, usually includes components that move relative to each other. For instance, a stapler may have a body portion that stores staples and an anvil. During a stapling procedure, the anvil is caused to move toward the body portion in order to clamp a section of tissue. When the section of tissue is adequately clamped between the body portion and the anvil, staples stored in the body portion are driven into the tissue and closed against the anvil. In order to ensure that the section of tissue is adequately clamped, and to ensure that the staples are properly closed, the relative positions of the components of the stapler, e.g., the body portion and the anvil, should to be known by the user of the stapler device.

U.S. patent application Ser. No. 09/723,715 filed on Nov. 28, 2000, which is incorporated in its entirety herein by reference, describes an electro-mechanical surgical system which includes a motor system, a control system and a remote control unit. A surgical instrument (e.g., a surgical attachment such as a surgical stapler) connects either fixedly or detachably to a distal end of a flexible shaft. A proximal end of the flexible shaft connects to a housing which encloses the motor system. Rotatable drive shafts are disposed with the flexible shaft and are rotated by the motor system. The remote control unit enables a user to control the motor system in accordance with software corresponding to the surgical instrument connected to the flexible shaft.

Surgical instruments, such as surgical staplers, may incorporate various control mechanisms, see, U.S. Pat. No. 5,915,616 to Viola et al. and U.S. Pat. No. 5,609,285 to Grant et al., to ensure the proper positioning and firing of the circular surgical stapler. Other conventional control and sensing mechanisms for use with surgical instruments include lasers, proximity sensors and endoscopes, see, U.S. Pat. No. 5,518,164 to Hooven and U.S. Pat. No. 5,573,543 to Akopov et al. Additional control features described may assist the surgeon in ensuring that the firing of the staples corresponds to the approach of the anvil toward the body portion. A number of conventional circular surgical staplers attached to a shaft are manipulated and actuated using hand held controls, see, U.S. Pat. No. 4,705,038 to Sjostrem; U.S. Pat. No. 4,995,877 to Ams et al., U.S. Pat. No. 5,249,583 to Mallaby, U.S. Pat. No. 5,383,880 to Hooven, and U.S. Pat. No. 5,395,033 to Byrne et al.

When a surgical instrument, e.g., a surgical stapler, is connected to a drive shaft of a surgical system such as described above, it may be important that the components of the surgical instrument, e.g., the anvil, anvil stem and body portion, are properly calibrated in order to ensure proper functioning in conjunction with the control system. If the components are not properly calibrated, errors may occur in the operation of the surgical instrument and consequently the control system may lose its effectiveness. Furthermore, a variety of different types of surgical instruments may be used with the electro-mechanical device described above.

Thus, there is a need to provide a calibration system and method that provides improved effectiveness in calibrating the components of a surgical instrument.

It is therefore an object of the present invention to provide a calibration system and method that provides improved effectiveness in calibrating the components of a surgical instrument.

It is another object of the present invention to provide a calibration system and method that enables different types of surgical instruments attached to an electro-mechanical surgical system to be calibrated.

SUMMARY OF THE INVENTION

According to one example embodiment of the present invention, a calibration system for a surgical instrument is provided. The calibration system may include an actuator, such as a motor system and flexible shaft. The calibration system may also include a surgical instrument having a first component actuatable by the actuator and a second component, the first component disposed in a first position relative to the second component. The calibration system may also include a sensor configured to provide a signal corresponding to a movement of the actuator, and calibration data corresponding to the surgical instrument. In addition, the calibration system includes a processor configured to process the calibration data and the signal from the sensor for determining, upon actuation of the actuator, a second position of the first component relative to the second component.

In one example embodiment of the present invention, the sensor is a Hall-effect sensor and the processor is configured to determine the second position of the first component relative to the second component in accordance with a number of rotations of the rotatable drive shaft. The calibration data may include data corresponding to a relative distance between the first component and the second component in the first position, e.g., the distance between the two components when the surgical instrument is in the fully-open or fully-closed position. In addition, the calibration data may include data correlating the movement of the actuator to a change in the relative position of the first component to the second component, e.g., correlating the number of number of rotations of a rotatable drive shaft to a change in the distance between the components of the surgical instrument. The calibration data may also include a correction factor stored in the memory unit of the surgical instrument, such that the processor is configured to determine the second position of the first component relative to the second component in accordance with the correction factor. The correction factor may correspond to a difference between an actual amount of actuation, e.g., an actual number of rotations of a drive shaft, and an expected amount of actuation, e.g., an expected number of rotations of the drive shaft, required to actuate the first component from the first position to the second position relative to the second component.

BRIEF DESCRIPTION OF THE DRAWINGS

FIG. 3($b$) is a diagram that illustrates schematically a memory unit in a remote power console, in accordance with one embodiment of the present invention;

DETAILED DESCRIPTION

Figure 1:
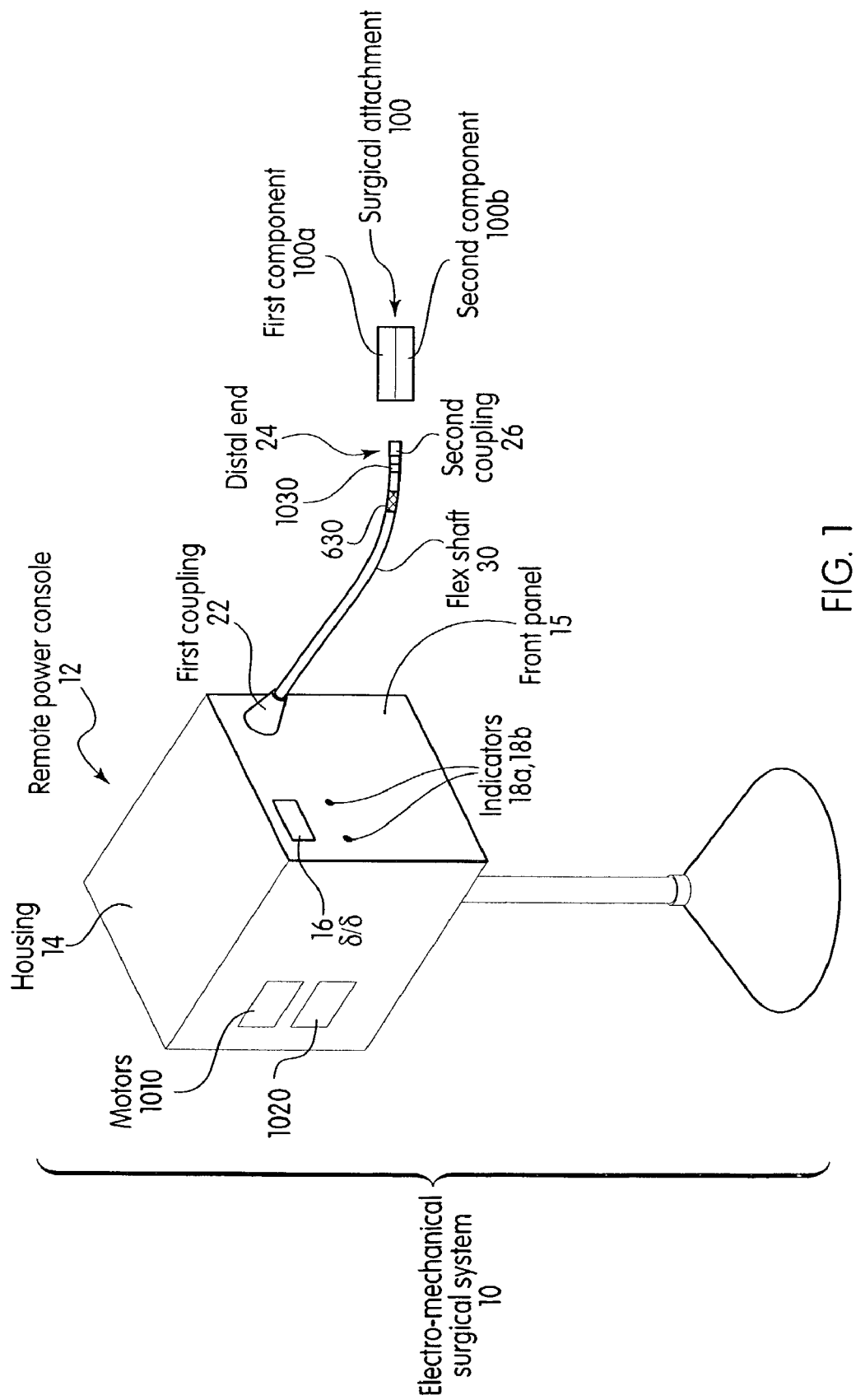
FIG. 1 is a perspective view of an electro-mechanical surgical system, according to one example embodiment of the present invention.

FIG. 1 is a perspective view of an electro-mechanical surgical system 10, according to one example embodiment of the present invention. The electro-mechanical surgical system 10 may include, for example, a remote power console 12, which includes a housing 14 having a front panel 15. Mounted on the front panel 15 are a display device 16 and indicators 18$a$, 18$b$. A flexible shaft 20 may extend from the housing 14 and may be detachably secured thereto via a first coupling 22. The distal end 24 of the flexible shaft 20 may include a second coupling 26 adapted to detachably secure a surgical instrument 100, e.g., a surgical attachment, to the distal end 24 of flexible shaft 20. Alternatively, the distal end 24 of the flexible shaft 20 may be adapted to fixedly secure the surgical instrument 100 to the distal end 24 of flexible shaft 20. The surgical instrument 100 may be, for example, a surgical stapler, a surgical cutter, a surgical stapler-cutter, a linear surgical stapler, a linear surgical stapler-cutter, a circular surgical stapler, a circular surgical stapler-cutter, a surgical clip applier, a surgical clip ligator, a surgical clamping device, a vessel expanding device, a lumen expanding device, a scalpel, a fluid delivery device or any other type of surgical instrument. Such surgical instruments are described, for example, in U.S. Pat. No. 6,315,184, entitled "A Stapling Device for Use with an Electromechanical Driver Device for Use with Anastomosing, Stapling, and Resecting Instruments," U.S. Pat. No. 6,443,973, entitled "Electromechanical Driver Device for Use with Anastomosing, Stapling, and Resecting Instruments," U.S. Pat. No. 6,264,087, entitled "Automated Surgical Stapling System," U.S. patent application Ser. No. 09/510,926, entitled "A Vessel and Lumen Expander Attachment for Use with an Electromechanical Driver Device," U.S. patent application Ser. No. 09/510,927, entitled "Electromechanical Driver and Remote Surgical Instruments Attachment Having Computer Assisted Control Capabilities," U.S. patent application Ser. No. 09/510,931, entitled "A Tissue Stapling Attachment for Use with an Electromechanical Driver Device," U.S. patent application Ser. No. 09/510,932, entitled "A Fluid Delivery Mechanism for Use with Anastomosing, Stapling, and Resecting Instruments," and U.S. patent application Ser. No. 09/510,933, entitled "A Fluid Delivery Device for Use with Anastomosing, Stapling, and Resecting Instruments," each of which is expressly incorporated herein in its entirety by reference thereto.

The remote power console 12 also includes a motor 1010 for driving the surgical instrument 100. In one example embodiment, the motor 1010 couples to the surgical instrument 100 via a rotatable drive shaft 630 within the flexible shaft 20. As the drive shaft 630 rotates, a first component 100$a$ of the surgical instrument 100 moves relative to a second component 100$b$ of the surgical instrument 100. For instance, depending on the type of surgical instrument that is used, actuation via the rotatable drive shaft 630 of the first component 100$a$ relative to the second component 100$b$ may, for example, include opening or closing a clamp, moving a cutting edge and/or firing staples or any other type of movement. Examples of such a remote power console 12 is described in U.S. patent application Ser. No. 09/723,715, entitled "Electro-Mechanical Surgical Device," and U.S. patent application Ser. No. 09/836,781, entitled "Electro-Mechanical Surgical Device," each of which is expressly incorporated herein by reference in its entirety. The power console 12 may also include a processor 1020.

Figure 2:
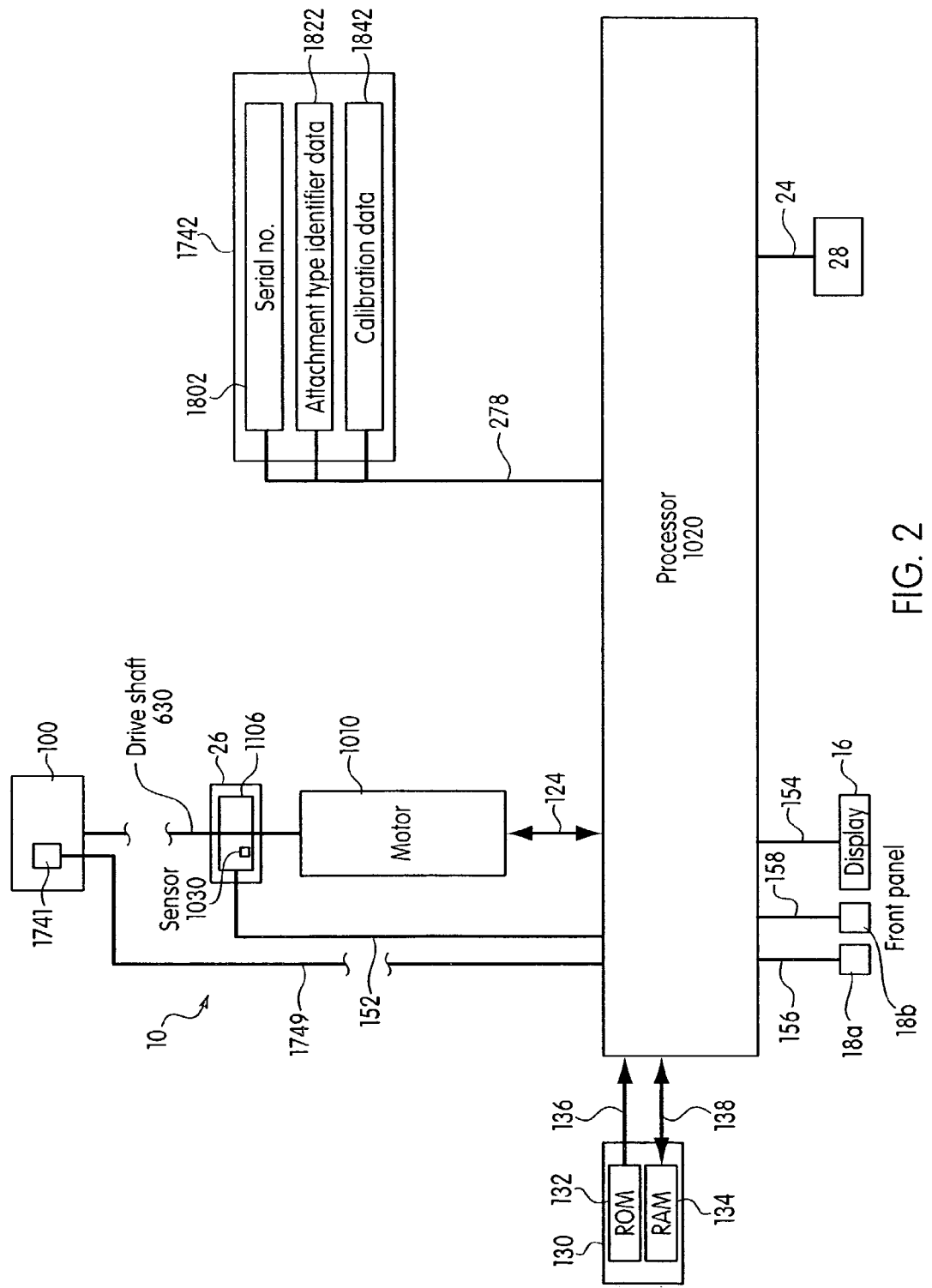
FIG. 2 is a diagram that shows schematically an electro-mechanical surgical system, in accordance with one embodiment of the present invention.

FIG. 2 is a diagram that shows schematically the electro-mechanical surgical system 10, in accordance with one embodiment of the present invention. The processor 1020 may be disposed in the remote power console 12, and is configured to control various functions and operations of the electro-mechanical surgical system 10. A memory unit 130 is provided and may include memory devices, such as, a ROM component 132 and/or a RAM component 134 for storing programs or algorithms employed by the processor 1020. The ROM component 132 is in electrical and logical communication with processor 1020 via line 136, and the RAM component 134 is in electrical and logical communication with processor 1020 via line 138. The RAM component 134 may include any type of random-access memory, such as, for example, a magnetic memory device, an optical memory device, a magneto-optical memory device, an electronic memory device, etc. Similarly, the ROM component 132 may include any type of read-only memory, such as, for example, a removable memory device, such as a PC-Card or PCMCIA-type device. It should be appreciated that the ROM component 132 and the RAM component 134 may be embodied as a single unit or may be separate units and that the ROM component 132 and/or the RAM component 134 may be provided in the form of a PC-Card or PCMCIA-type device.

The processor 1020 is further connected to the display device 16 via a line 154 and to the indicators 18a, 18b via respective lines 156, 158. The line 124 electrically and logically connects the processor 1020 to the motor 1010. The motor 1010 is coupled via the rotatable drive shaft 630 to the surgical instrument 100. A sensor 1030, which may include an encoder 1106, is electrically and logically connected to processor 1020 via line 152. The sensor 1030 may be disposed in the second coupling 26 of the flexible shaft 20 and may be configured to provide a signal corresponding to a movement of the drive shaft 630 via line 152 to the processor 1020. The surgical instrument 100 may include a memory unit 1741, an example of which is illustrated schematically in FIG. 3(a) and described in greater detail below, which is electrically and logically connected to the processor 1020 by a line 1749. The processor 1020 may also include an additional memory unit 1742, an example of which is illustrated schematically in FIG. 3(b) and described in greater detail below, which may be disposed within the remote power console 12 and which is electrically and logically connected to the processor 1020 by a line 278.

Figure 3A:
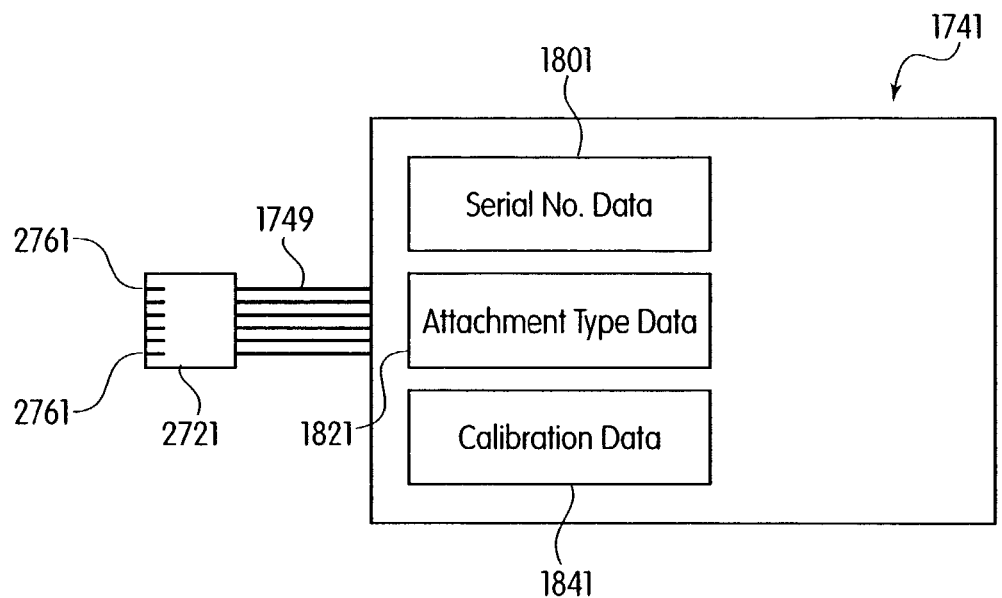
FIG. 3($a$) is a diagram that illustrates schematically a memory unit in a surgical instrument, in accordance with one embodiment of the present invention.

As mentioned above, according to one embodiment of the present invention, the surgical instrument 100 may include a memory unit, such as memory unit 1741 illustrated schematically in FIG. 3(a). The memory unit 1741 may store information as described, for example, in U.S. patent application Ser. No. 09/723,715, filed on Nov. 28, 2000, U.S. patent application Ser. No. 09/836,781, filed on Apr. 17, 2001, U.S. patent application Ser. No. 09/887,789, filed on Jun. 22, 2001, and U.S. patent application Ser. No. 10/099,634, filed on Mar. 15, 2002 each of which is expressly incorporated herein by reference in its entirety. For instance, as illustrated in FIG. 3(a), the memory unit 1741 may include a data connector 2721 that includes contacts 2761, each electrically and logically connected to memory unit 1741 via a respective line 1749. The memory unit 1741 may be configured to store, for example, serial number data 1801, attachment type identifier data 1821 and calibration data 1841. The memory unit 1741 may additionally store other data. Both the serial number data 1801 and the attachment type identifier data 1821 may be configured as read-only data. In the example embodiment, serial number data 1801 is data uniquely identifying the particular surgical instrument 100, whereas the attachment type identifier data 1821 is data identifying the type of the surgical instrument 100, such as, for example, a circular stapler. The calibration data 1841 may be any type of data used to calibrate the surgical instrument 100. For instance, the calibration data 1841 may include data correlating a movement of an actuator, e.g., a number of rotations of a rotatable drive shaft 630, to a change in the distance between the first component 100a and the second component 100b of the surgical instrument 100. Furthermore, the calibration data 1841 may include data corresponding to a position of first and second components of the surgical instrument relative to one another, such as a distance of the first component 100a of the surgical instrument 100 relative to the second component 100b when in a particular position, e.g., a fully-open or a fully-closed position. In addition, the calibration data 184 may include a correction factor, as more fully described below, in order to account for gearing backlash or other types of mechanical variables of the particular type of surgical instrument 100. Generally, the calibration data 184 may provide any type of data corresponding to any mechanical variable specific to the particular surgical instrument 100.

Figure 3B:
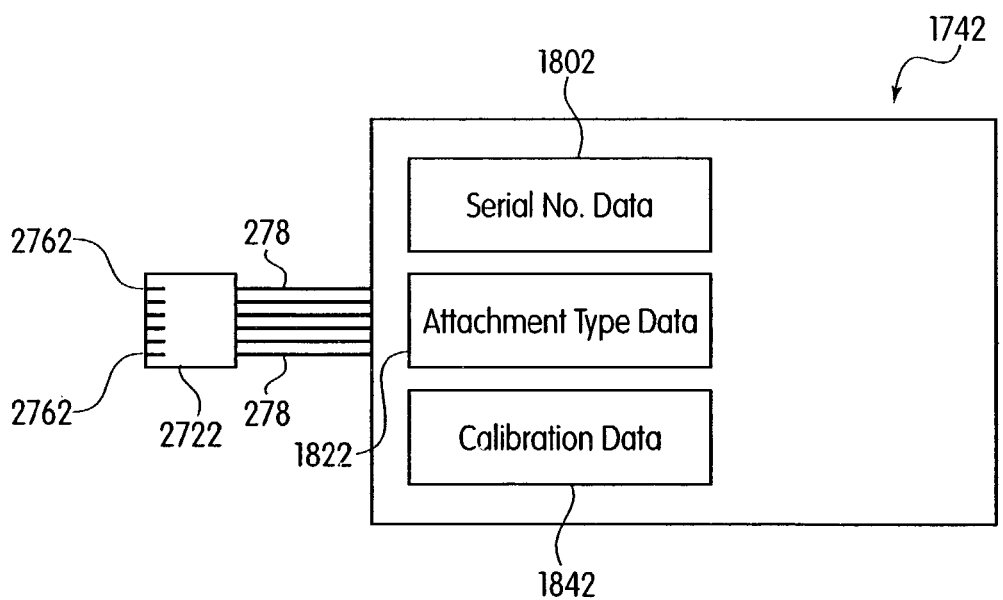

As mentioned above, according to one embodiment of the present invention, the remote power console 14, e.g., the processor 1020 may also include a memory unit, such as memory unit 1742 illustrated schematically in FIG. 3(b). It should be understood that, while the memory unit 1742 is shown as being discrete, some or all of the data stored thereby may alternatively be stored in the memory unit 130. Referring to FIG. 3(b), the memory unit 1742 may include a data connector 2722 that includes contacts 2762, each electrically and logically connected to the memory unit 1742 via a respective line 278. The memory unit 1742 may be configured to store, for example, serial number data 1802, attachment type identifier data 1822 and calibration data 1842 for a number of different surgical attachments. The memory unit 1742 may additionally store other data. Both the serial number data 1802 and the attachment type identifier data 1822 may be configured as read-only data. In the example embodiment, serial number data 1802 is data uniquely identifying particular surgical instruments, whereas the attachment type identifier data 1822 is data identifying various types of surgical instruments, such as, for example, a circular stapler. The calibration data 1842 may be any type of data used to calibrate a surgical instrument. For instance, the calibration data 1842 may include data correlating a movement of an actuator, e.g., a number of rotations of a rotatable drive shaft 630, to a change in the distance between the first component 100a and the second component 100b of the surgical instrument 100. Furthermore, the calibration data 1842 may include data corresponding to a position of first and second components of the surgical instrument relative to one another, such as a distance of the first component 100a of the surgical instrument 100 relative to the second component 100b when in a particular position, e.g., a fully-open or a fully-closed position. As stated above with respect to calibration data 1841, the calibration data 1842 may provide any type of data corresponding to any mechanical variable specific to a surgical instrument 100.

Referring to FIG. 2, the electro-mechanical surgical system 10 may also include the sensor 1030. The sensor 1030 is connected to the processor 1020 via a line 152. The sensor 1030 may provide signals related to the movement of actuators, e.g., rotation of the drive shaft 630, within the flexible shaft 20. In one embodiment, the sensor 1030 is positioned at the distal end 24 of the flexible shaft 20. For instance, according to one example embodiment of the present invention, the sensor 1030 includes a first encoder 1106 provided within the second coupling 26 and configured to output a signal in response to and in accordance with the rotation of the first drive shaft 630. The signal output by the encoder 1106 may represent the rotational position of the rotatable drive shaft 630 as well as the rotational direction thereof. The encoder 1106 may be, for example, a Hall-effect device, an optical devices, etc. Although the encoder 1106 is described as being disposed within the second coupling 26, it should be appreciated that the encoder 1106 may be provided at any location between the motor 1010 and the surgical instrument 100. It should be appreciated that providing the encoder 1106 within the second coupling 26 or at the distal end 24 of the flexible shaft 20 provides for an accurate determination of the drive shaft rotation. If the encoder 1106 is disposed at the proximal end of the flexible shaft 20, windup of the rotatable drive shaft 630 may result in measurement error.

Figure 4:
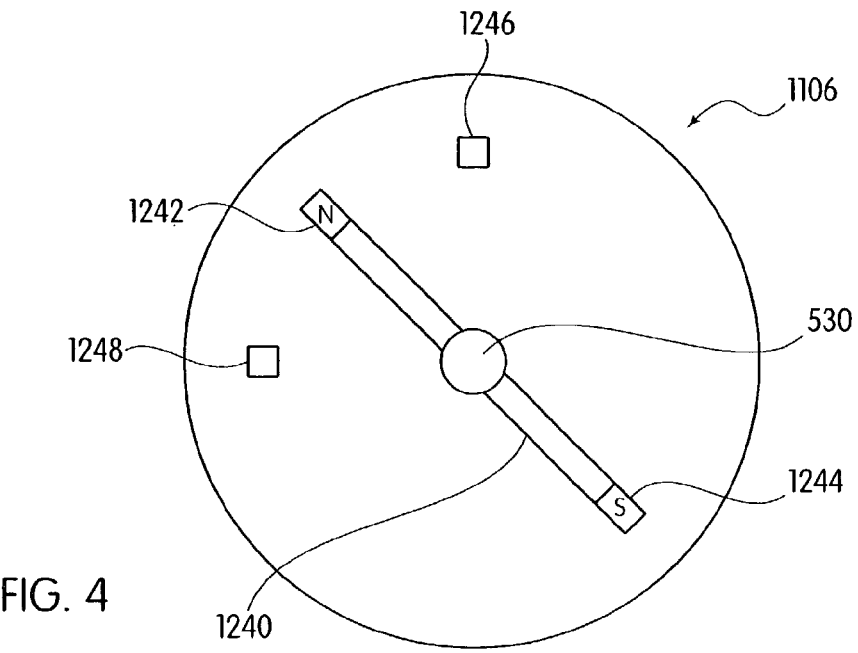
FIG. 4 is a schematic view of an encoder, which includes a Hall-effect device, in accordance with one embodiment of the present invention.

FIG. 4 is a schematic view of an encoder 1106, which includes a Hall-effect device. Mounted non-rotatably on drive shaft 630 is a magnet 240 having a north pole 242 and a south pole 244. The encoder 1106 further includes a first sensor 246 and second sensor 248, which are disposed approximately 90° apart relative to the longitudinal, or rotational, axis of drive shaft 630. The output of the sensors 246, 248 is persistent and changes its state as a function of a change of polarity of the magnetic field in the detection range of the sensor. Thus, based on the output signal from the encoder 1106, the angular position of the drive shaft 630 may be determined within one-quarter revolution and the direction of rotation of the drive shaft 630 may be determined. The output of the encoder 1106 is transmitted via a respective line 152 to processor 1020. The processor 1020, by tracking the angular position and rotational direction of the drive shaft 630 based on the output signal from the encoder 1106, can thereby determine the position and/or state of the first component 100a of the surgical instrument 100 relative to the second component 100b. That is, by counting the revolutions of the drive shaft 630, the processor 1020 can determine the position and/or state of the first component 100a of the surgical instrument relative to the second component 100b.

Figure 5:
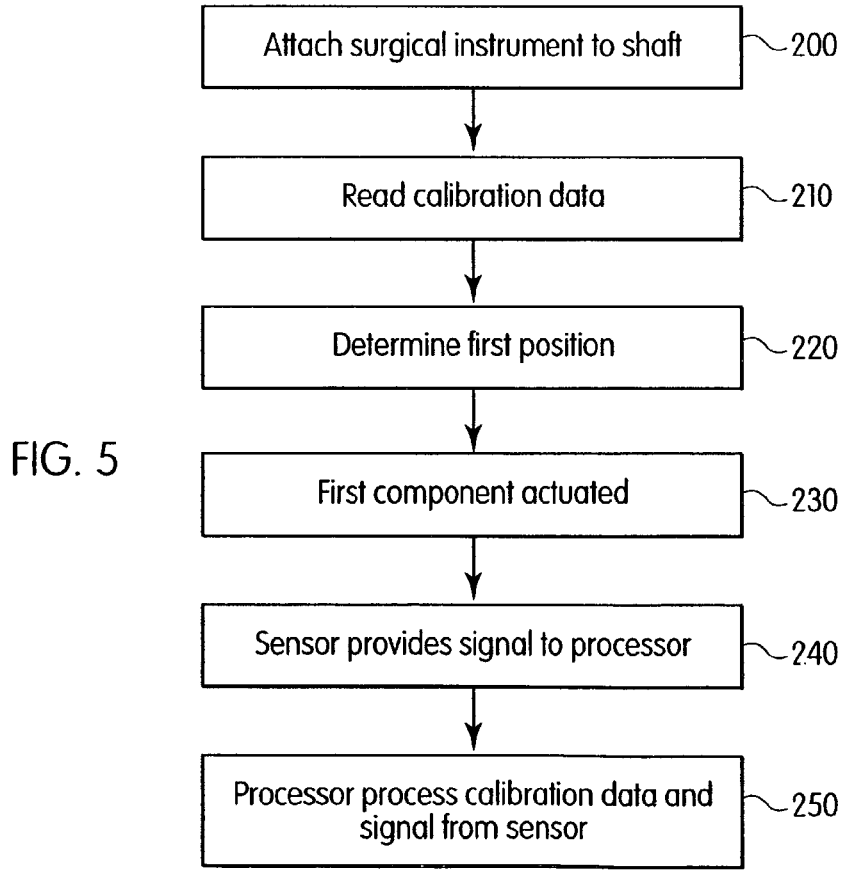
FIG. 5 is a flowchart that illustrates a method for calibrating a surgical instrument, in accordance with one example embodiment of the present invention.

FIG. 5 is a flowchart that illustrates a method for calibrating a surgical instrument 100, in accordance with one example embodiment of the present invention. At step 200, a user attaches the surgical instrument 100 to the distal end 24 of the flexible shaft 20. At step 210, the processor 1020 reads calibration data corresponding to the surgical instrument 100. The calibration data corresponding to the surgical instrument 100 may be calibration data 1841 stored in the memory unit 1741 in the surgical instrument 100 and may be provided to the processor 1020 via line 1749 after attachment of the surgical instrument 100 to the flexible shaft 20. Alternatively, the calibration data may be calibration data 1842 stored in the memory unit 1742 of the remote power console 12 or in any other data storage location. In another embodiment, attachment type identifier data 1821 corresponding to the surgical instrument 100 is stored in the memory unit 1741 in the surgical instrument 100, and calibration data corresponding to more than one different type of surgical instrument may be stored as calibration data 1842 in a memory unit 1742 in the remote power console 12—after attachment of the surgical instrument 100 to the flexible shaft 20, the processor 1020 is configured to read the attachment type identifier data 182 of the surgical instrument 100, to identify the type of surgical instrument that has been attached, and to select from the calibration data 1842 of the memory unit 1742 the calibration data corresponding to the particular surgical instrument being used.

At step 220, the processor 1020 determines a first position of the surgical instrument 100, e.g., a first position of the first component 100a of the surgical instrument 100 relative to the second component 100b. For example, the processor 1020 may determine a distance between the first component 100a and the second component 100b in the first position. This first position may be, for example, a position employed during shipping of the surgical instrument 100, e.g., a fully-open or a fully-closed position. In one embodiment, one or both of the calibration data 1841, 1842 corresponding to the surgical instrument 100 includes data corresponding to the distance between the first and second components 100a, 100b of the surgical instrument 100 when in the first position, thereby enabling the processor 1020 to determine the first position of the first component 100a of the surgical instrument 100 relative to the second component 100b by merely reading one or both of the calibration data 1841, 1842 corresponding to the surgical instrument 100.

At step 230, the first component 100a of the surgical instrument 100 is actuated so as to move relative to the second component 100b. The actuation of the first component 100a at step 230 may be for the purposes of clamping a section of tissue, for driving staples, etc., depending on the type of surgical instrument being used. In one embodiment, the first component 100a of the surgical instrument 100 is actuated relative to the second component 100b by the motor 1010 rotating the rotatable drive shaft 630 in the flexible shaft 20.

At step 240, the sensor 1030 provides a signal to the processor 1020 corresponding to the movement of the actuator. For instance, the sensor 1030 may be a Hall-effect sensor that provides a signal corresponding to the number of rotations that has been made by the rotatable drive shaft 630, as described more fully above. At step 250, the processor 1020 may process the data corresponding to the first position of the first component 100a relative to the second component 100b, the signal received from the sensor 1030, and one or both of the calibration data 1841, 1842 corresponding to the surgical instrument 100 in order to determine a second position of the first component 100a of the surgical instrument 100 relative to the second component 100b. For instance, where either of the calibration data 1841, 1842 includes data correlating a number of rotations of the rotatable drive shaft 630 to a change in the distance between the first component 100a and the second component 100b of the surgical instrument 100, the processor 1020 may determine from the signal provided by the Hall-effect sensor 1030 the distance traveled by the first component 100a relative to the second component 100b. Where either of the calibration data 1841, 1842 also includes an initial distance between the first and second components 100a, 100b in the first position, the processor 1020 may determine the difference between the initial distance between the first and second components 100a, 100b and the distance traveled by the first component 100a during step 230 in order to ascertain the actual distance between the first and second components 100a, 100b after the first component 100a has been actuated. Thus, the surgical instrument 100 may be calibrated thereby ensuring that the relative position of the first and second components 100a, 100b are known during operation of the surgical instrument 100, and the position of the surgical instrument 100, e.g., the position of the first component 100a relative to the second component 100b, may be monitored during operation.

Figure 6:
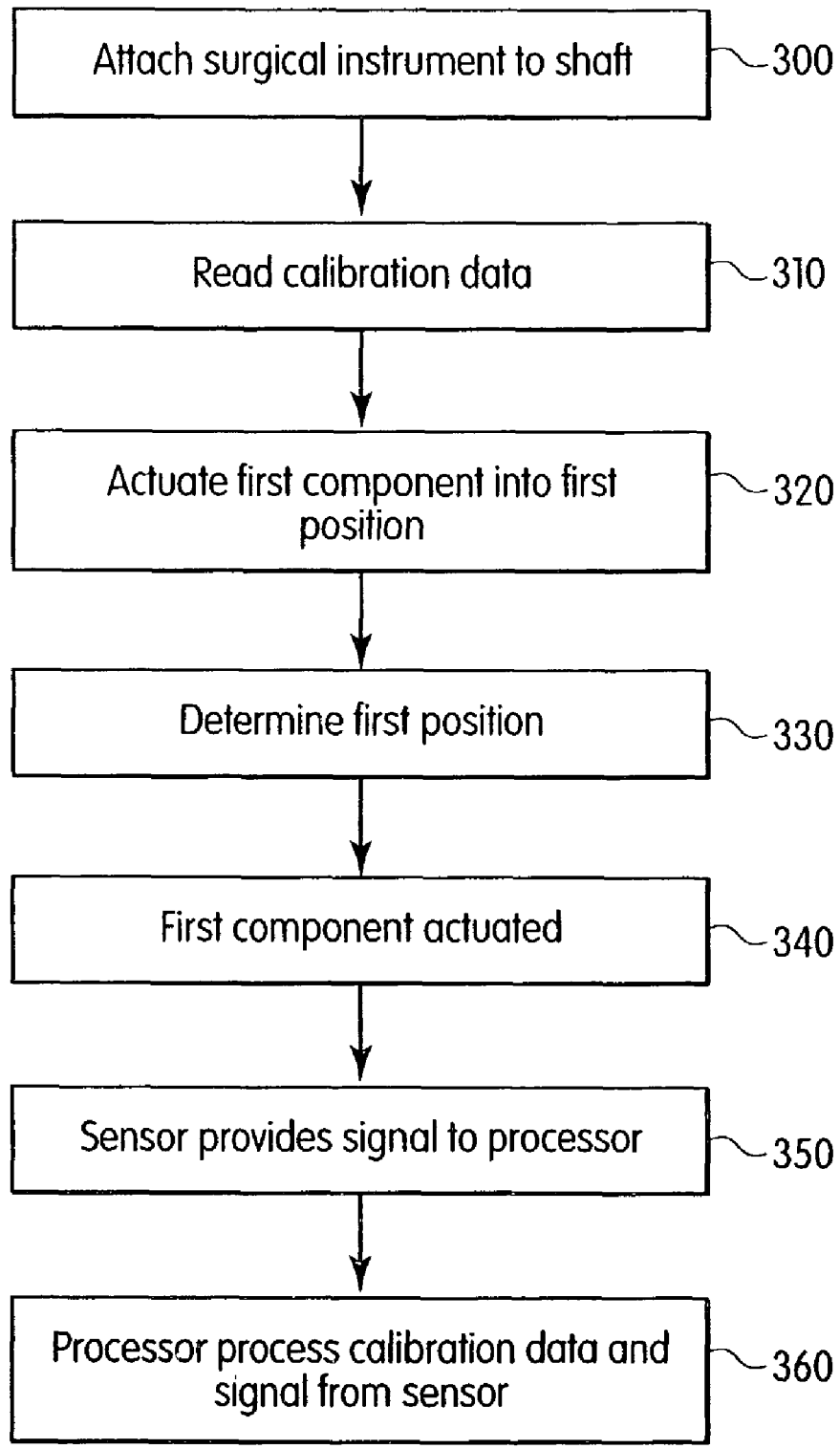
FIG. 6 is a flowchart that illustrates a method for calibrating a surgical instrument, in accordance with another example embodiment of the present invention.

FIG. 6 is a flowchart that illustrates a method for calibrating a surgical instrument 100, e.g., a 55 mm linear stapler/cutter surgical attachment, in accordance with another example embodiment of the present invention. At step 300, a user attaches the surgical instrument 100 to the distal end 24 of the flexible shaft 20. At step 310, the processor 1020 reads calibration data corresponding to the surgical instrument 100. As described above, the calibration data corresponding to the surgical instrument 100 may be the calibration data 1841 stored in the memory unit 1741 of the surgical instrument 100 and may be provided to the processor 1020 via line 120 upon attachment of the surgical instrument 100 to the flexible shaft 20, or may be the calibration data 1842 stored in the memory unit 1742 of the remote power console 12 or in any other data storage location.

At step 320, the first component 100a is either automatically or selectively actuated into a first position relative to the second component 100b upon the surgical instrument 100 being connected to the flexible shaft 20. For instance, upon the surgical instrument 100 being connected to the flexible shaft 20, the first component 100a may be actuated relative to the second component 100b into a fully-open or a fully-closed position. This fully-open or fully-closed position may be a "hard-stop" position, e.g., a position past which the first component 100a is mechanically unable to travel. The processor 1020 may detect when the first component 100a of the surgical instrument 100 reaches the first position when, for example, the drive shaft 630 is unable to further rotate, or after the expiration of a predetermined time period.

At step 330, the processor 1020 determines a first position of the first component 100a of the surgical instrument 100 relative to the second component 100b. For example, the processor 1020 may determine a distance between the first and second components 100a, 100b in the first position. As previously mentioned, one or both of the calibration data 1841, 1842 corresponding to the surgical instrument 100 may include data corresponding to the distance between the first and second components 100a, 100b of the surgical instrument 100 when in the first position, thereby enabling the processor 1020 to determine the first position of the first component 100a of the surgical instrument 100 relative to the second component 100b by merely reading one or both of the calibration data 1841, 1842 corresponding to the surgical instrument 100.

At step 340, the first component 100a of the surgical instrument 100 is again actuated so as to move relative to the second component 100b. The actuation of the first component 100a at step 340 may be for the purpose of clamping a section of tissue, for firing staples, etc., depending on the type of surgical instrument being used. In one embodiment, the first component 100a of the surgical instrument 100 is actuated relative to the second component 100b by the motor 1010 rotating the rotatable drive shaft 630 of the flexible shaft 20.

At step 350, the sensor 1030 provides a signal to the processor 1020 corresponding to the movement of the actuator, e.g., a signal corresponding to the number of rotations that has been made by the rotatable drive shaft 630, as described more fully above. At step 360, the processor 1020 may process the data corresponding to the first position of the first component 100a relative to the second component 100b, the signal received from the sensor 1030, and one or both of the calibration data 1841, 1842 corresponding to the surgical instrument 100 in order to determine a second position of the first component 100a of the surgical instrument 100 relative to the second component 100b. For instance, the processor 1020 may determine from the signal provided by the Hall-effect sensor 1030 the distance traveled by the first component 100a relative to the second component 100b during step 340, and may further determine the difference between the initial distance between the first and second components 100a, 100b in the first position. Thus, the processor 1020 may also determine the distance traveled by the first component 100a during step 340, in order to ascertain the actual distance between the first and second components 100a, 100b after the first component 100a has been actuated.

The method described by the flowchart of FIG. 6 may be used even when a surgical instrument 100 is calibrated, e.g., moved to a fully open or fully closed position, prior to packaging and shipping. For instance, although a surgical instrument 100 is calibrated prior to packaging and shipping, the surgical instrument 100 may be subjected to vibration or shock prior to use, thereby causing the components of the surgical instrument to be moved from their original calibrated positions. The method of FIG. 6 may be used to ensure that the processor 1020 may accurately determine the relative positions of the components of the surgical instrument 100 even if the components are inadvertently moved prior to their use.

In one embodiment of the present invention, a correction factor is used when calibrating the surgical instrument 100. A correction factor may be any type of calibration data corresponding to a surgical instrument. For instance, a correction factor may correspond to a difference between expected calibration data of a typical surgical instrument and actual calibration data of a particular surgical instrument of that type. Such a correction factor may be employed to account for gearing backlash or any other mechanical variables that may be distinct to a particular surgical instrument.

For instance, a surgical instrument 100 may be packaged with a first component 100a, e.g., an anvil, in contact with a solid mechanical buffer that defines a first, fully-open position. In the first, fully-open position of a surgical instrument 100, the first component 100a may be positioned at a distance of, e.g., 16 mm, from the second component 100b. The surgical instrument 100 may also have a second, fully-closed position in which the first component 100a is positioned at a distance of, e.g., 1 mm, from the second component 100b. The memory unit 1742 of the remote power console 12 may include calibration data 1842 that correlates the expected movement of an actuator to the relative movement of the components 100a, 100b. For instance, the memory unit 1742 of the remote power console 12 may include calibration data 1842 that correlates an expected number of rotations of drive shaft 630 to a change in the linear distance between the first and second components of the surgical instrument 100. In this example, the memory unit 1742 of the remote power console 12 may include calibration data 1842 that correlates 550 rotations of drive shaft 630 to a 15 mm change in the linear distance between the first and second components 100a, 100b of the surgical instrument 100. Thus, the calibration data 1842, when read by the processor 1020, may instruct the processor 1020 to rotate the rotatable drive shaft 630 a total of 550 times in order to close the jaws of the surgical instrument 100 from a first, fully-open position to a second, fully-closed position. However, the correction factor accounts for the situation in which, while 550 turns may be required to fully close the components 100a, 100b of a typical surgical instrument of this type, a particular surgical instrument may require a different number of turns of the drive shaft 630 in order to fully close the components 100a, 100b.

Figure 7:
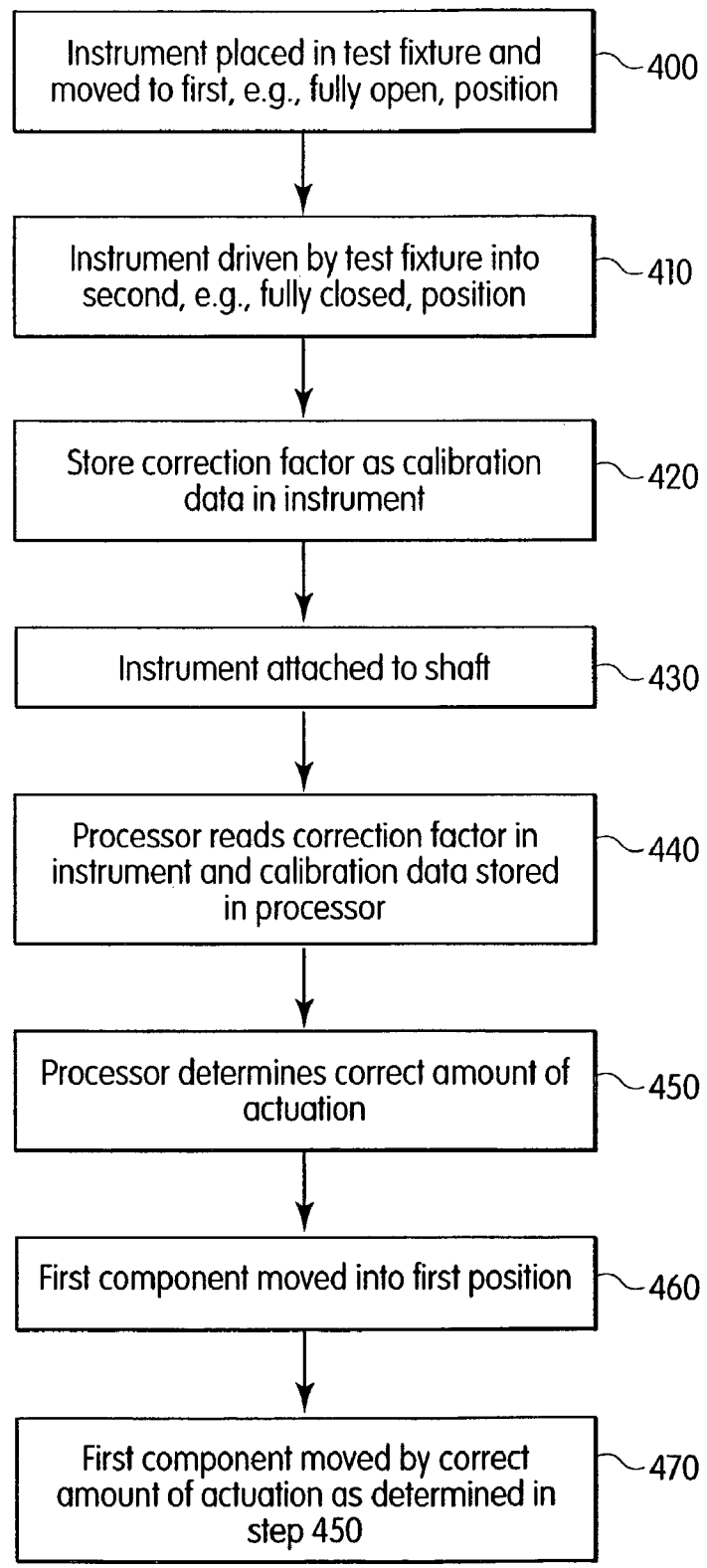
FIG. 7 is a flowchart that illustrates a method for calibrating a surgical instrument using a correction factor, in accordance with one embodiment of the present invention.

FIG. 7 is a flowchart that illustrates a method for calibrating a surgical instrument 100 using a correction factor, in accordance with one embodiment of the present invention. At step 400, a particular surgical instrument 100 is placed in a test fixture, e.g., during manufacture, and opened to a first, fully-open position. The surgical instrument 100 may be opened by the test fixture at a speed and torque equivalent to speed and torque at which the surgical instrument 100 will be driven when connected to the flexible shaft 20 of the remote power console 12. At step 410, the test fixture drives the surgical instrument 100 to the second, fully-closed position. However, instead of the 550 turns required to fully close the components 100a, 100b of a typical surgical instrument of this type, this particular surgical instrument 100 may require a different number of turns, e.g., 562, of the drive shaft 630 in order to fully close the components 100a, 100b.

At step 420, a correction factor equal to the difference between the expected number of turns required to fully close the components 100a, 100b in a typical surgical instrument and the actual number of turns required to fully close the components 100a, 100b in the particular surgical instrument 100 is stored as a correction factor in the calibration data 1841 in the memory unit 1741 of the surgical instrument 100. At step 430, the surgical instrument 100 is attached to the flexible shaft 20. At step 440, the processor 1020 reads the correction factor from the memory unit 1741 in the surgical instrument 100. In addition, the processor 1020 may read the calibration data 1842 stored in the memory unit 1742 of the remote power console 12, which may store the expected number of turns required for a typical surgical instrument of the same type as the surgical instrument 100.

At step 450, the processor 1020 determines, from the calibration data 1842 stored in the memory unit 1742 in the remote power console 12 and from the correction factor stored as calibration data 1841 in the memory unit 1741 in the surgical instrument 100, the correct amount of actuation, e.g., the correct number of turns of the drive shaft 630, that is required to move the first and second components 100a, 100b a desired distance relative to each other. For instance, in the above example, in order to move the first and second components 100a, 100b from the first, fully-open position to the second, fully-closed position, the processor 1020 may add the expected calibration data 1842 stored in the memory unit 1742 of the remote power console 12, e.g., 550 turns, to the correction factor stored in the memory unit 1741 of the surgical instrument 100, e.g., 12 turns, to determine that the correct number of turns required to move the first and second components 100a, 100b between the fully-open and fully-closed positions is 562 turns. Of course, the processor 1020 may also use the calibration data 1842 and the correction factor to determine the correct number of turns required to move the first and second components 100a, 100b any distance relative to each other. In addition, it should be understood that other types of correction factors, stored in other data storage locations, may also be employed by the system 10.

At step 460, the first component 100a is moved into the first, fully-open position relative to the second component 100b, so as to prepare for operation. Alternatively, the surgical instrument 100 may be shipped having the first component 100a in the fully-open position relative to the second component 100b. At step 470, the first component 100a is actuated from the fully-open position to the fully-closed position, or is actuated to any desired position relative to the second component 100b, by rotating the drive shaft 630 the number of turns determined in step 450.

Figure 8:
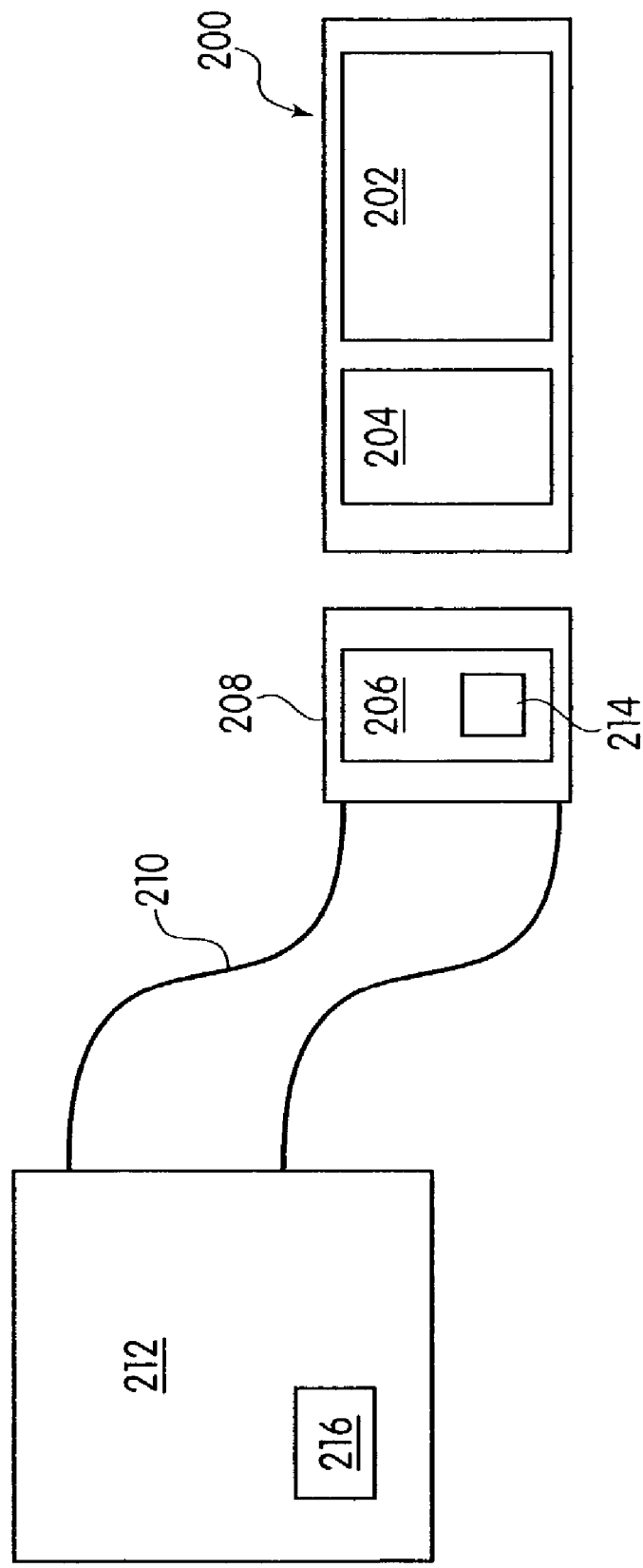
FIG. 8 is a diagram that illustrates schematically an esophageal expander surgical instrument having a strain gauge, in accordance with one embodiment of the present invention.

The above method may also be used with an esophageal expander surgical instrument that may use a strain gauge to measure esophageal compression. FIG. 8 is a diagram that illustrates schematically an esophageal expander surgical instrument 200 having a strain gauge 202. Mounted strain gauges may require calibration, e.g., of gain and offset. Correction factors associated with the gain and offset may be derived during the final assembly of an esophageal expander surgical instrument, and may be stored electronically in a memory device 204 contained within the esophageal expander surgical instrument 200. The strain gauge 202 may also use a signal-conditioning amplifier 206. The signal-conditioning amplifier 206 may be located in an adapter 208 for a flexible shaft 210 or in a power console 212. The signal-conditioning amplifier 206 also may require calibration, e.g., of gain and offset. The signal-conditioning amplifier 206 may include a memory device 214 to store its respective correction factors. Accordingly, when an esophageal expander surgical instrument 200 is coupled to a flexible drive shaft 210, a processor 216 in the remote power console 212 may read the stored calibration data from the memory devices 204, 214 in the esophageal expander surgical instrument 200 and in the signal-conditioning amplifier 206, respectively, and use the correction factors to calibrate the esophageal expander surgical instrument 200 prior its operation.

Several example embodiments of the present invention are specifically illustrated and/or described herein. However, it will be appreciated that modifications and variations of the present invention are covered by the above teachings without departing from the spirit and intended scope of the present invention.

What is claimed is:

1. A system for calibrating a surgical instrument comprising:
    an electro-mechanical actuator including a memory unit storing at least predetermined calibration data for a number of different surgical instruments;
    a surgical instrument of the number of surgical instruments actuatable by the electro-mechanical actuator, the surgical instrument having first and second components that are moveable relative to each other;
    each surgical instrument including a memory unit storing at least predetermined calibration data corresponding to the surgical instrument, wherein the calibration data corresponds to a position of the surgical instrument, the position of the surgical instrument being a position of the first and second components relative to each other, wherein the calibration data includes a correction factor that corresponds to a difference between an actual amount of actuation required to actuate the surgical instrument from a first position to a second position, and an expected amount of actuation required to actuate the surgical instrument from the first position to the second position; and
    a processor configured to determine a position of the surgical instrument in accordance with at least one of the predetermined calibration data of the electro-mechanical actuator and the predetermined calibration data of the surgical instrument.

2. The system of claim 1, further comprising:
    a sensor configured to provide a signal corresponding to a movement of the actuator, wherein the processor is further configured to process the signal from the sensor for determining a position of the surgical instrument.

3. The system of claim 2, wherein the sensor is a Hall-effect sensor.

4. The system of claim 1, wherein the calibration data includes data corresponding to a relative distance between a first component and a second component of the surgical instrument.

5. The system of claim 1, wherein the calibration data includes data correlating a movement of the actuator to a change in position of the surgical instrument.

6. The system of claim 1, wherein the surgical instrument includes a memory unit storing identification data, the processor being configured to select, upon receiving the identification data corresponding to the surgical instrument, the calibration data corresponding to the surgical instrument.

7. The system of claim 1, wherein the surgical instrument is one of automatically and selectively actuated to a first position upon being attached to the actuator.

8. The system of claim 1, wherein the processor is configured to determine a position of the surgical instrument in accordance with the correction factor.

9. A system for calibrating a surgical instrument comprising:
    an electro-mechanical actuator including a memory unit storing at least calibration data for a number of different surgical instruments;
    a surgical instrument of the number of different surgical instruments actuatable by the electro-mechanical actuator;

each surgical instrument including a memory unit storing at least calibration data corresponding to the surgical instrument; and a processor configured to determine a position of the surgical instrument in accordance with at least one of the calibration data of the electro-mechanical actuator and the calibration data of the surgical instrument;

wherein the calibration data stored in the memory unit of the surgical instrument includes a correction factor;

wherein the actuator includes a motor and a rotatable drive shaft couplable to the surgical instrument and the motor; and wherein the correction factor corresponds to a difference between an actual number of rotations of a drive shaft required to actuate the surgical instrument from a first position to a second position, and an expected number of rotations of a drive shaft required to actuate the surgical instrument from the first position to the second position.

10. A method for calibrating a surgical instrument of a number of different surgical instruments each being attachable to an actuator, the surgical instrument having first and second components that are moveable relative to each other, comprising the steps of:

providing to a processor predetermined calibration data and a correction factor stored in a memory unit of the surgical instrument and corresponding to one surgical instrument of the number of surgical instruments and predetermined calibration data stored in the actuator corresponding to the one surgical instrument of the number of surgical instruments, wherein the calibration data corresponds to a position of the surgical instrument, the position of the surgical instrument being a position of the first and second components relative to each other;

determining the correction factor by determining the difference between an actual amount of actuation required to actuate the surgical instrument from a first position to a second position, and an expected amount of actuation required to actuate the surgical instrument from the first position to the second position; and determining, via the processor, the position of the surgical instrument in accordance with the predetermined calibration data of at least one of the actuator and the surgical instrument.

11. The method of claim 10, further comprising the step of:
providing to the processor a signal corresponding to a movement of the actuator;
determining, via the processor, the position of the surgical instrument in accordance with the signal.

12. The method of claim 10, wherein the surgical instrument includes a first component and a second component,
the processor determining a position of the first component relative to the second component.

13. The method of claim 10, wherein the calibration data includes a relative distance between a first component and a second component.

14. The method of claim 10, further comprising the step of:
providing a signal, via a sensor, corresponding to a movement of the actuator.

15. The method of claim 10, wherein the step of providing calibration data includes providing data correlating a movement of the actuator to a change in the position of the surgical instrument.

16. The method of claim 10, wherein the step of providing calibration data includes providing calibration data stored in a memory unit of the processor.

17. A method for calibrating a surgical instrument attachable to an actuator, comprising the steps of:

providing to a processor calibration data corresponding to the surgical instrument; and determining, via the processor, a position of the surgical instrument;

wherein the step of providing calibration data includes providing calibration data stored in a memory unit of the surgical instrument;

wherein the step of providing calibration data stored in a memory unit of the surgical instrument includes providing a correction factor;

further comprising the step of:

actuating the surgical instrument by a motor via a rotatable drive shaft couplable to the surgical instrument and the motor, wherein the step of determining the correction factor includes determining a difference between an actual number of rotations of a drive shaft required to actuate the surgical instrument from a first position to a second position, and an expected number of rotations of a drive shaft required to actuate the surgical instrument from the first position to the second position.

* * * * *